(12) United States Patent
Barnicki et al.

(10) Patent No.: US 6,582,565 B1
(45) Date of Patent: Jun. 24, 2003

(54) RECOVERY OF 3,4-EPOXY-1-BUTENE BY EXTRACTIVE DISTILLATION

(75) Inventors: Scott Donald Barnicki, Kingsport, TN (US); Robert Sterling Kline, Talbott, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 10/052,043

(22) Filed: Jan. 17, 2002

(51) Int. Cl.[7] .................. B01D 3/40; C07D 301/32
(52) U.S. Cl. ................. 203/64; 203/57; 203/58; 203/60; 203/62; 203/63; 203/70; 549/541
(58) Field of Search ............... 203/57, 58, 60, 203/62, 63, 64, 70; 549/241, 541

(56) References Cited

U.S. PATENT DOCUMENTS

| | | | |
|---|---|---|---|
| 4,897,498 A | 1/1990 | Monnier et al. | |
| 4,950,773 A | 8/1990 | Monnier et al. | |
| 5,000,825 A | * 3/1991 | Shih et al. | 203/3 |
| 5,129,996 A | * 7/1992 | Shih | 203/64 |
| 5,362,890 A | 11/1994 | Stavinoha et al. | |
| 5,618,954 A | 4/1997 | Boeck et al. | |
| 5,945,550 A | 8/1999 | Barnicki et al. | |

OTHER PUBLICATIONS

Perry et al, Chemical Engineers' Handbook, 5th. Ed., p. 13–43 to 13–44 (1973).*
H. Z. Kister, Distillation Design, McGraw Hill, N.Y. (1992), Chapter 6.
H. Z. Kister, Distillation Design, McGraw Hill, N.Y. (1992), Chapter 8.
Roal et al, Phase Equilibria, 1998, pp. 39–55.

* cited by examiner

Primary Examiner—Zinna Northington Davis
(74) Attorney, Agent, or Firm—Michael J. Blake; Bernard J. Graves, Jr.

(57) ABSTRACT

Disclosed is a process for the recovery and purification of 3,4-epoxy-1-butene (epoxybutene) from mixtures comprising epoxybutene and aliphatic and aromatic hydrocarbons containing five to seven carbon atoms having boiling points between about 20° C. and 115° C. by means of extractive distillation of the epoxybutene using certain extractive distillation solvents.

9 Claims, 1 Drawing Sheet

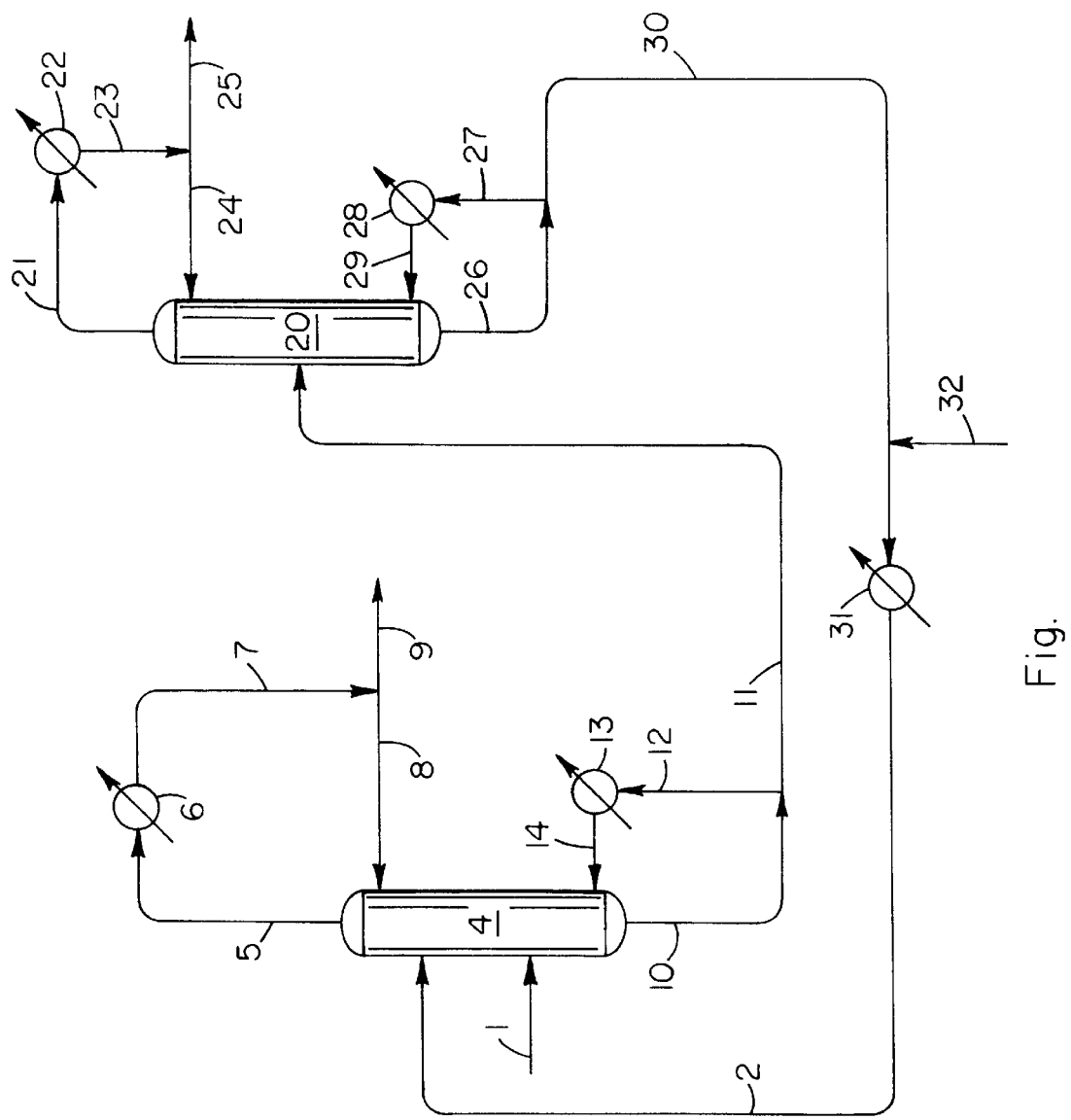

RECOVERY OF 3,4-EPOXY-1-BUTENE BY EXTRACTIVE DISTILLATION

FIELD OF THE INVENTION

This invention relates to a process for the recovery and purification of 3,4-epoxy-1-butene (epoxybutene). More specifically, the present invention relates to the separation by extractive distillation of epoxybutene from crude mixtures with close-boiling, pinched, or azeotrope-forming compounds. The invention disclosed herein is of particular interest and utility in the recovery and purification of epoxybutene from mixtures comprising aliphatic and aromatic hydrocarbons containing five to seven carbon atoms having boiling points between about 20° C. and 11 5° C.

DESCRIPTION OF PRIOR ART AND BACKGROUND OF INVENTION

U.S. Pat. Nos. 4,897,498, 4,950,773, and 5,618,954 disclose gas phase epoxidation processes for the production of epoxybutene from molecular oxygen and 1,3-butadiene using silver-based catalysts. U.S. Pat. No. 5,362,890 describes a gas-phase epoxidation process for the production of epoxybutene in which a C2 to C6 paraffinic hydrocarbon is used as gas-phase reaction diluent in order to improve heat transfer and increase the safe oxygen levels in the epoxidation reactor. These patents further disclose that liquid 1,3-butadiene and liquid n-butane/1,3-butadiene mixtures are particularly favorable solvents for the absorptive recovery of epoxybutene from the gaseous effluent of the epoxidation reactor. An epoxide-rich absorbent obtained from the bottom of the absorption column typically comprises 1 to 40 mole percent epoxybutene, 1 to 10 mole percent water, and 30 to 98 mole percent n-butane and 1,3-butadiene. This epoxide-rich absorbent is subjected to further processing steps, i.e., decantation and distillations in order to recover substantially pure epoxybutene and n-butane and 1,3-butadiene that is substantially free of epoxybutene, i.e., less than 5000 ppm by volume of epoxybutene. Since n-butane and 1,3-butadiene have normal boiling points of 0° C. and −2° C., respectively, and do not form close-boiling, pinched, or azeotropic mixtures with epoxybutene, the distillation separations disclosed therein can be accomplished in simple single feed rectification columns.

U.S. Pat. No. 5,945,550 discloses a gas-phase epoxidation process for the production of epoxybutene in which one or more C4 to C10 paraffinic hydrocarbons having high autoiginition temperatures are used as gas-phase reaction diluents in order to improve heat transfer, increase the safe oxygen levels, and substantially increase space-time yield in the epoxidation reactor. Although clearly advantageous for improving reactor performance, many of such C5 to C7 alkane diluents having boiling points between about 20° C. and about 115° C. form close-boiling, pinched, or azeotropic mixtures with epoxybutene. Such mixtures are not amenable to production of epoxybutene in high purity and high recovery in simple single-feed rectification columns.

Furthermore, many alkyl and aryl hydrocarbons, with boiling points between about 20° C. and about 115° C., are useful as absorbents for the recovery of epoxybutene from gas-phase reactor effluents, as extractants of epoxybutene from aqueous streams, and as reaction media for further derivatization of epoxybutene. Examples of such alkyl and aryl hydro-carbons include but are not limited to benzene, toluene, isopentane, n-pentane, n-hexane, n-heptane, and 2,2-dimethylbutane. These compounds also form close-boiling, pinched, or azeotropic mixtures with epoxybutene and thus cannot be separated effectively in simple single-feed rectification columns. Thus there is a need for a process to effectively separate such compounds from epoxybutene.

Relative volatility, α, is defined as the ratio of the equilibrium vapor and liquid compositions of the two components to be separated. Thus, $$\alpha = \frac{\frac{y_1}{x_1}}{\frac{y_2}{x_2}} \tag{1}$$

where $y_i$ is the mole fraction of component i in the vapor phase and $x_i$ is the mole fraction of the component i in the liquid phase. The normal convention in the art is to define the lower boiling pure component as component 1 and the higher boiling pure component as component 2.

In an azeotropic system, the relative volatility will vary from greater than unity to less than unity as one passes through the azeotropic composition. At mole fractions of the lower boiling component less than the azeotropic composition the relative volatility is greater than unity, while at mole fractions greater than the azeotropic composition the relative volatility is less than unity. At the azeotropic composition, the relative volatility of the components forming the azeotrope is unity. In other words, the vapor and liquid compositions are identical. Since distillation works by differences in vapor and liquid compositions, no further separation is possible by simple distillation once the azeotropic composition is reached, even with an infinite number of equilibrium stages.

In a pinched or close-boiling binary system that shows positive deviations from ideal liquid behavior, the relative volatility will vary from greater than unity at low concentrations of the lower boiling component to close to unity at high concentrations of the lower boiling component. Thus, near the pinch point, the composition of the vapor and liquid phases approach each other, and a large number of equilibrium stages is required for further separation.

Table I shows the effect of relative volatility (α) on theoretical stage requirements in terms of the number of theoretical equilibrium stages required at total reflux for the given degree of separation or purity. In Table I, Separation Purity refers to the mole fraction separation purity of both products.

TABLE I

| Separation Purity | Relative Volatility | | | | | | | |
|---|---|---|---|---|---|---|---|---|
| | 1.00 | 1.02 | 1.1 | 1.2 | 1.4 | 1.5 | 2.0 | 3.0 |
| | Theoretical Stages at Total Reflux | | | | | | | |
| 0.999 | ∞ | 697 | 144 | 75 | 40 | 33 | 19 | 12 |
| 0.995 | ∞ | 534 | 110 | 57 | 30 | 25 | 14 | 9 |
| 0.990 | ∞ | 463 | 95 | 49 | 26 | 22 | 12 | 7 |
| 0.98 | ∞ | 392 | 81 | 42 | 22 | 18 | 10 | 6 |
| 0.95 | ∞ | 296 | 61 | 31 | 16 | 14 | 8 | 4 |
| 0.90 | ∞ | 221 | 45 | 23 | 12 | 10 | 5 | 3 |

Rarely is it economical or practical to operate a distillation column with more than about 60 theoretical (typically 70 to 120 actual stages). Thus, for situations where both high purity and high recovery are required, the relative volatility should be greater than about 1.2.

Extractive distillation is a method of separating close boiling, azeotropic, or pinched compounds from each other by conducting the distillation in a two-feed, multi-staged, rectification column in the presence of an added liquid or liquid mixture, said liquid(s) having a boiling point higher than the compounds being separated. The extractive agent or solvent is introduced near the top of the column, above the primary feed stage where the components to be separated are introduced. Since the extractive agent is chosen to be higher boiling than the components to be separated, the agent remains largely in the liquid phase throughout the sections of the column below the stage upon which it is fed. Extractive distillation operates by the exploitation of the selective solvent-induced enhancements or moderations of the liquid-phase nonidealities of the components to be separated. The solvent selectively alters the activity coefficients of the components being separated, thus making a greater degree of separation possible than in the absence of the extractive agent. At the bottom of the extractive distillation column, the less volatile component in the presence of the selected solvent and the extractive distillation solvent itself are removed continuously from the column. The usual methods of separation of these two components are by a second single feed distillation, cooling and phase separation, or solvent extraction. Although the principles of extractive distillation are well-known in the art, there are no a piori methods of determining the efficacy of extractive agents for a given separation, even for those ordinarily skilled in the art.

The usual method of evaluating the efficacy of extractive distillation agents is to measure the change in relative volatility of the compounds to be separated in the absence and presence of the extractive distillation agent. A practical method of measuring relative volatility is with an equilibrium still. A given composition of components 1 and 2 is charged to the still pot, heated to the boiling point, and allowed to come to vapor-liquid equilibrium. Samples of the vapor and liquid are taken, analyzed to determine the composition, and these measurements are used to calculate the relative volatility. To test the efficacy of a solvent, the experiment is repeated with solvent added to the still pot as well as a mixture of the two components to be separated. Each potential extractive distillation agent is evaluated at a constant component 1 to component 2 weight ratio and constant solvent to component 1/component 2 weight ratio.

The present invention provides an extractive distillation process or method that enhances the relative volatility between epoxybutene and aliphatic and aromatic hydrocarbons containing five to seven carbon atoms and having boiling points between about 20 and 115° C. to improve the rectification efficiency over that of a single-feed distillation column or reactive distillation column. The process of the invention utilizes organic compounds that are stable, and can be separated from epoxybutene and the hydrocarbon(s) and recycled to the extractive distillation column with little decomposition. In its broader aspects, the present invention provides a process for the separation of epoxybutene from a mixture comprising epoxybutene and at least one aliphatic or aromatic hydrocarbon containing five to seven carbon atoms and having a boiling point of between about 20 and 115° C. which comprises the steps of:

(1) feeding a mixture comprising epoxybutene and at least one hydrocarbon selected from aliphatic or aromatic hydrocarbons containing five to seven carbon atoms and having boiling points of between about 20 and 115° C., to the mid-section of an extractive distillation column;

(2) feeding an extractive distillation solvent to the upper section of the extractive distillation column;

(3) removing from the upper section or top of the extractive distillation column a vapor comprising the hydrocarbon;

(4) removing from the lower section or base of the extractive distillation column a liquid comprising epoxybutene and extractive distillation solvent; and (5) separating the liquid of step (4) into epoxybutene and extractive distillation solvent; wherein the extractive distillation solvent (i) is inert, i.e. is non-reactive with respect to epoxybutene and the hydrocarbon, (ii) does not form an azeotrope with either epoxybutene or the hydrocarbon, (iii) is miscible with epoxybutene and the hydrocarbon, (iv) has a boiling point at least about 20° C. higher than the higher boiling point of epoxybutene and the hydrocarbon, and (v) creates a large relative volatility difference between epoxybutene and the hydrocarbon, i.e., in mixtures of epoxybutene, the hydrocarbon and the extractive distillation solvent.

In a preferred embodiment of the invention, the separation of step (5) comprises the steps of:

(5) feeding the liquid comprising epoxybutene and the extractive distillation solvent removed from the lower section or bottom of the distillation column in step (4) to the mid-section of a solvent recovery distillation column;

(6) removing from the upper section or top of the solvent recovery distillation column a vaporous distillate product comprising greater than about 99.5 weight percent epoxybutene; and (7) removing from the lower section or bottom of the solvent recovery distillation column a liquid comprising the extractive distillation solvent.

BRIEF DESCRIPTION OF THE DRAWINGS

The accompanying FIGURE is a process flow diagram illustrating an epoxybutene separation system embodying the principles of the processes of the present invention. While the present invention is susceptible to embodiment in various forms, there is shown in the FIGURE and hereinafter described in detail preferred embodiments of the invention. However, the present disclosure is to be considered as an exemplification of the invention without limitation to the specific embodiments illustrated.

DETAILED DESCRIPTION

The process of the present invention may be used in combination with any process wherein a mixture of epoxybutene and one or more aliphatic and/or aromatic hydrocarbons containing five to seven carbon atoms are generated. The epoxidation processes described in U.S. Pat. Nos. 5,362,890 and 5,945,550 are typical of the reaction effluents that may be employed. The pressures referred to herein are given in bars absolute (bara). The terms extractive distillation agent and solvent are used interchangeably herein. As used herein, the general term hydrocarbon refers to any aliphatic or aromatic hydrocarbon, including mixtures thereof, containing five to nine carbon atoms or any other component that may boil close to, pinch, or azeotrope with epoxybutene.

In accordance with the present invention, a mixture comprising, as majority constituents, epoxybutene and at least one hydrocarbon selected from aliphatic or aromatic hydrocarbons containing five to seven carbon atoms and having boiling points of between about 20 and 115° C., is fed to the mid-section of an extractive distillation column. The epoxybutene/hydrocarbon feed mixture may comprise any ratio of epoxybutene:hydrocarbon, e.g., from about 0.1 to about 99.9 mole percent epoxybutene and 0.1 to 99.9 mole percent hydrocarbon. More typical feeds used in the process, such as the organic layer of an epoxybutene-rich liquid effluent obtained from an epoxybutene absorber, contain about 5 to 30 mole percent epoxybutene and about 50 to 95 mole percent hydrocarbon, less than 1 mole percent dissolved water, and less than about 1 mole percent of other components such as butenediols, crotonaldehyde, epoxybutene oligomers, nitrogen, oxygen, carbon dioxide, and argon.

As noted above, characteristics of the extractive distillation solvents which may be used in the present invention include (i) inertness, i.e. the solvents are essentially non-reactive with respect to either the epoxybutene and the hydrocarbon, (ii) non-azeotrope forming with either epoxybutene or the hydrocarbon, (iii) miscibility with both epoxybutene and the hydrocarbon, (iv) a boiling point at least about 20° C. higher than the highest boiling point possessed by epoxybutene or the hydrocarbon, and (v) the ability to create a large relative ($\alpha$) volatility difference between epoxybutene and the hydrocarbon, i.e., in mixtures of epoxybutene, the hydrocarbon and the extractive distillation solvent. We have found that the following classes of compounds are exemplary solvents for the present invention: C2 to C8 diols; C3 to C12 to alcohols, e.g., C3 to C12 alkanols; C5 to C12 ketones, e.g., aliphatic ketones containing 5 to 12 carbon atoms; alkyl alkanoate esters containing a total of 6 to 12 carbon atoms, C6 to C12 aliphatic and cyclic ethers; glycol ethers, e.g., mono- and di-alkyl glcol ethers containing a total of 4 to 12 carbon atoms; glycol ether esters, e.g., alkanoate esters of mono-alkyl glycol ethers containing a total of 5 to 12 carbon atoms; and polar, aprotic solvents, e.g., N-heterocyclic compounds, C2 to C6 nitriles, carboxylic acid amides containing a total of 4 to 12 carbon atoms, lactams, and dialkyl sulfoxides, and mixtures thereof.

Specific examples of suitable solvents include, but are not limited to, 1-methyl-2-pyrrolidinone (NMP), pyridine, ethylene glycol, 1,2-propylene glycol, 1,3-propylene glycol, 3-butene-1,2-diol (1,2-diol), 2-butene-1,4-diol (1,4-diol), 1,2-butanediol, 1,3-butanediol, 1,4-butanediol, dimethylformamide, dimethylacetamide, diethylformamide, diethylacetamide, acetonitrile, dimethylsulphoxide, morpholine, dibutylether, diisobutylether, diethylene glycol dimethyl ether, triethylene glycol dimethyl ether, tetraethylene glycol dimethyl ether, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether, ethylene glycol monoethyl ether acetate, ethylene glycol monobutyl ether acetate, ethylene glycol monopropyl ether acetate, propylene glycol monomethyl ether acetate, propylene glycol monoethyl ether acetate, propylene glycol monopropyl ether acetate, 2-heptanone (MAK), 3-heptanone, 4-heptanone, 6-methyl-2-hexanone (MIAK), methylisobutylketone, diisopropylketone, dipropylketone, dibutylketone, cyclohexanone, diisobutylketone, isobutyl isobutyrate, n-butyl propionate, isobutyl propionate, n-propyl butyrate, isopropyl butyrate, isopropyl isobutyrate, n-butyl butyrate, 2-ethylhexyl acetate, methyl benzoate, isopentyl acetate, n-pentyl acetate, n-butyl acetate, propanol, n-butanol, n-pentanol, 2-pentanol, 3-pentanol, n-hexanol, cyclohexanol, 2,2,4-trimethyl-1,3-pentandiol, and mixtures thereof. The preferred extractive distillation solvents are alkyl alkanoate esters containing 6 to 8 carbon atoms, C6 to C8 aliphatic ketones, C6 to C8 glycol ether acetates, more preferably 4-methyl-2-pentanone, 2-heptanone, 5-methyl-2-hexanone, n-butyl acetate, and propylene glycol monomethyl ether acetate (1-methoxy-2-propyl acetate).

The amount of extractive distillation solvent fed to the extractive distillation column can vary substantially depending on, for example, the particular vessel configuration, the use of packing material and its type, and the feed rate and composition of the epoxybutene/hydrocarbon feed. Generally, the mass ratio of the extractive distillation solvent feed to the epoxybutene/hydrocarbon feed mixture is in the range of about 10:1 to about 1:3, more typically about 5:1 to 1:1. The temperature of the extractive distillation solvent (stream 2) normally is in the range of about 0 to 100° C., more preferably about 20 to 70° C. The extractive distillation solvent is fed to the upper section of the extractive distillation column above the point at which the epoxybutene/hydrocarbon is fed and a few stages from the top of the column. The extractive distillation solvent preferably is fed at least 2 theoretical equilibrium stages from the top of extractive distillation column. The section above the extractive distillation solvent feed point serves as a rectifying section to keep the solvent out of the distillate. Preferably, the section of the extractive distillation column between the epoxybutene/hydrocarbon feed and the extractive distillation solvent feed comprises at least 3 theoretical equilibrium stages, more preferably 5 to 35 stages. Preferably, the section of the extractive distillation column below the epoxybutene/hydrocarbon feed comprises at least two theoretical equilibrium stages, more preferably 4 to 20 stages. The preferred number of total theoretical equilibrium stages in column 4 is 7 to 50 stages, more preferably 10 to 35 stages. The temperature at the top stage of the column is normally from about 10 to 90° C., depending the operating pressure of the column. The temperature at the base of the column typically is about 100 to 240° C., more typically about 100 to 180° C. The operating pressure of the extractive distillation column normally is within the range of about 0.1 to 4 bara, and preferably from about 0.8 to 2.0 bara.

The vapor obtained from the upper section or top of the extractive distillation column typically comprises at least 98 weight percent, preferably at least 99 weight percent, hydrocarbon and less than about 0.5 weight percent epoxybutene, preferably less than about 0.1 epoxybutene. The vapor stream may contain minor amounts, e.g., up to about 2 weight percent, of other materials such as water, nitrogen, oxygen, argon, and carbon dioxide. The liquid product removed from the lower section or base of the extractive distillation column comprises epoxybutene and extractive distillation solvent, typically a solution of about 5 to 60 weight percent, more typically about 10 to 40 weight percent, epoxybutene in the extractive distillation solvent.

In accordance with the second embodiment of the present invention, the liquid product removed from the lower section or base of the extractive distillation column epoxybutene may be fed to a solvent recovery column wherein the epoxybutene is distilled from the extractive distillation solvent. More specifically, the liquid product from the extractive distillation column normally is fed to the mid-section of a solvent recovery column. The solvent recovery column typically comprises 3 to 20, preferably 5 to 12, theoretical equilibrium stages. The conditions employed within the column can vary depending on a number of factors such as the particular apparatus and extractive distillation solvent employed. The temperature at the top stage of the column normally is about 40 to 90° C. depending on the operating pressure of the column. The temperature at or near the base of the solvent recovery column normally is about 100 to 240° C., preferably from about 100 to 180° C., depending on the extractive distillation solvent chosen. The operating pressure within the column normally is about 0.1 to about 2 bara, and preferably from about 0.15 to about 1.0 bara.

The conditions within the solvent recovery column are adjusted to provide for the removal from the lower section or base of the solvent recovery column a liquid product stream comprising at least 99.5 weight percent, preferably at least 99.8 weight percent, extractive distillation solvent and less than 0.5 weight percent, preferably less than 0.2 weight percent, epoxybutene. An epoxybutene-rich vaporous distillate, typically containing at least about 99.0 weight percent epoxybutene, is removed from the upper section or top of the solvent recovery column.

With reference to the FIGURE, an epoxybutene/hydrocarbon feed mixture is fed via line 1 to the middle section of extractive distillation column 4, preferably at least two theoretical equilibrium stages above the bottom of column 4. An extractive distillation solvent is fed to the upper section of the extractive distillation column 4 via line 2, above the feed point of stream 1 and a few stages from the top of column 4. As noted above, the solvent stream 2 preferably is fed at least 2 theoretical equilibrium stages from the top of distillation column 4. A vaporous distillate product is removed from the top of column 4 via line 5 and is cooled in condenser 6 by indirect contact with any typical cooling media such as cooling water, chilled brine, or glycol. A portion of the condensed overhead vapors comprising hydrocarbon, e.g., a hydrocarbon such as 2-methylbutane having a purity of at least 98 weight percent, is conveyed via conduits 7 and 8 as reflux to the upper section of column 4. The preferred reflux ratio is between 0.5 and 5, more preferably between 1 and 2.5, and is adjusted to give the preferred hydrocarbon composition purity in the vapor product of conduit 5. A second portion of the hydrocarbon liquid is removed from the recovery system via line 9 and may be recycled to the production or extraction process wherein the hydrocarbon is utilized.

A liquid comprising extractive distillation solvent and epoxybutene is removed from the bottom of column 4 via line 10 and is fed via line 11 to a solvent recovery column, described in greater detail below, wherein epoxybutene is substantially separated from the accompanying solvent for recycle to column 4. A portion of the column underflow is diverted through line 12 to reboiler 13 and the heated liquid is returned to the lower section or base of column 4 through conduit 14.

The solvent/epoxybutene mixture from the bottom of column 4 is conveyed via lines 10 and 11 to solvent recovery distillation column 20, wherein epoxybutene is recovered from the extractive distillation solvent. Stream 11 is fed near the middle, e.g., about half way from the top, of column 20. A vaporous distillate product is removed from the top of column 20 via line 21 and is cooled in condenser 22 by indirect contact with any typical cooling media such as cooling water, chilled brine, or glycol. A portion of the condensed overhead vapors, typically comprising greater than 99.5 weight percent epoxybutene, is conveyed via conduits 23 and 24 as reflux to the upper section of column 20. A second portion of the condensed liquid is removed from the recovery system via conduit 25, e.g., to product storage. The preferred reflux ratio is between 0.5 to 8, more preferably 1.5 to 5.

The liquid solvent stream removed from the bottom of column 20 through line 26 is returned to extractive distillation column 4 via line 30, heat exchanger 31 and line 2. This liquid stream typically comprises at least 99.5 weight percent, preferably at least 99.8 weight percent, extractive distillation solvent. Stream 26 may be heat-interchanged with stream 11 to improve the energy efficiency of the process. A portion of the column underflow is diverted through line 27 to reboiler 28 and the heated liquid is returned to the lower section or base of column 20 through conduit 29. Stream 30 may be heat-interchanged with stream 11 to improve the energy efficiency of the process. Make-up solvent may be supplied via line 32. The temperature of stream 30 may be further adjusted by trim heat exchanger 31 to give the desired temperature of the solvent feed 2 in the range of about 0 to 100° C., more preferably about 20 to 70° C.

The extractive distillation column 4 and solvent recovery column 20 typically comprise columnar, pressure vessels containing trays or a packing material that facilitates intimate gas/liquid contact. The gas/liquid contacting equipment in the columns may include, but is not limited to, cross-flow sieve, valve, or bubble cap trays, structured packings such as Mellapak®, Flexipac®, Gempak®, Goodloe®, Sulzer®, or random or dumped packing, such as berl saddles, Intalox® saddles, raschig rings, Pall® rings, and Nutter Rings™. These and other types of suitable gas/liquid contacting equipment are described in detail in Kister, H. Z. Distillation Design, McGraw-Hill, N.Y. (1992), Chapters 6 and 8 the disclosures of which are incorporated herein by reference.

EXAMPLES

The operation of our novel process is further illustrated by the following examples. The efficacy of a particular component for altering the relative volatility of a binary azeotropic or binary pinch system under extractive distillation conditions can be determined by comparing the relative volatility of the binary pair at a given composition in the absence of the candidate agent to the relative volatility of the pair in the presence of a high concentration of the candidate agent. Effective extractive agents will significantly alter the relative volatility of the binary system (either up or down).

Comparative Example 1

A standard solution of epoxybutene and 2-methylbutane was prepared by mixing 1 part by weight epoxybutene with 1 part by weight 2-methylbutane. Approximately 40 grams of this standard solution was charged to an isobaric recirculating-type Khortum equilibrium still. Such a device is commonly used to measure vapor-liquid equilibrium and several similar embodiments are described in greater detail in Raal and Muhlbauer in *Phase Equilibria*, Taylor & Francis publishers, 1998, pages 39–55. The Khortum recirculating equilibrium still consisted of a glass-jacketed still body and vapor head space. Heat was provided by a heat transfer fluid circulating between the still body jacket and a constant temperature thermostatted bath. The generated vapors were conveyed via a jacketed glass tube from the head space of the still to a glass water-cooled condenser. Condensed vapors were then returned by gravity feed to the still body via a glass tube to a point below the liquid level in the still body. The still body and vapor head space were both fitted with K-type thermocouples for temperature measurement. The generated vapors were allowed to recirculate until equilibrium was reached, signified by a constant temperature reading for at least thirty minutes. Equilibrium was reached generally after about 3 hours. At this point small liquid and condensed vapor samples were collected and analyzed by gas chromatography to determine vapor and liquid compositions. The relative volatility of the mixture was 1.61.

Examples 1–10

Candidate extractive distillation agents were screened in the following fashion using the Khortum still described above. Approximately 15 grams of the standard epoxybutene/2-methyl-butane mixture along with approximately 20 grams of a candidate extractive distillation agent were charged to the circulation-type equilibrium still described above. The system was allowed to reflux for about three and one half hours while approaching equilibrium. A condensed vapor and a liquid sample were obtained and analyzed by a gas chromatograph (GC) with a thermal conductivity detector. The relative volatility in the presence of the candidate solvent was calculated from the GC composition data. The results of the relative volatility calculations are summarized in Table II for candidate solvent tested.

TABLE II

| Example No. | Extractive Distillation Solvent | Relative Volatility |
| --- | --- | --- |
| C-1 | None | 1.61 |
| 1 | 5-Methyl-2-Hexanone | 5.83 |
| 2 | 1-Methoxy-2-Propanol | 4.20 |
| 3 | 1-Methoxy-2-Propyl Acetate | 3.38 |
| 4 | 1,4-Dioxane | 4.22 |
| 5 | 4-Methyl-2-Pentanone | 3.59 |
| 6 | 2,4-Dimethyl-3-Pentanone | 2.47 |
| 7 | Butyl Acetate | 3.05 |
| 8 | n-Butanol | 2.92 |
| 9 | 2,2,5,5-Tetramethyltetrahydrofuran | 1.87 |
| 10 | Dibutyl Ether | 1.81 |

Comparative Example 2

This example demonstrates the poor separability of 2-methylbutane and oxybutene in the absence of an extractive distillation solvent. A mixture containing approximately 20 volume percent 2-methylbutane and 80 volume percent epoxybutene was fed continuously to plate 25 (counting from the bottom) of a 65-plate, 1-inch diameter, vacuum jacketed Oldershaw column. The column was fitted with a 500 ml glass reboiler flask and boil-up was provided by a 500-watt electric resistive heating mantle fitted to the reboiler. Overhead vapors were condensed in a glass double-condenser (coolant jacket and interior coil) provided with a continuous supply of ice-chilled water. Reflux was provided by a magnetically-controlled, plunger-type, glass reflux head. The reflux timer was set to return condensed material to the column for 4 seconds out of every 12 seconds, or at a reflux ratio of 2 to 1. Overhead product was collected continuously in a refrigerated receiver flask maintained at 0° C. The bottoms (column base) product was pumped continuously from the reboiler flask to a receiver flask maintained at cooling water temperature of about 17° C. The overhead and bottoms products were analyzed by gas chromatography to determine the compositions. The resultant compositions and fractional recoveries and separations, representative of steady state operation are given in Table 3.

Examples 11–13

Examples 11–13 demonstrate the improved separability of the 2-methylbutane and epoxybutene in the presence of selected extractive distillation solvents. For Examples 11 through 13, a mixture containing approximately 20 volume percent 2-methylbutane and 80 volume percent epoxybutene (Feed 1) was fed continuously to plate 25 (counting from the bottom) of a 65 plate 1-inch diameter vacuum jacketed Oldershaw column. Three different extractive distillation solvents, corresponding to Examples 11, 12, and 13 (Feed 2), were fed on stage 55 at a Feed 2:Feed 1 volume ratio of about 0.86. The column was fitted with a 500 ml glass reboiler flask and boil-up was provided by a 500-watt electric resistive heating mantle fitted to the reboiler. Overhead vapors were condensed in a glass double-condenser (coolant jacket and interior coil) provided with a continuous supply of ice-chilled water. Reflux was provided by a magnetically-controlled, plunger-type, glass reflux head. The reflux timer was set to return condensed material to the column for 4 seconds out of every 12 seconds, or at a reflux ratio of 2 to 1. Overhead product was collected continuously in a refrigerated receiver flask maintained at 0° C. The bottoms (column base) liquid product was pumped continuously from the reboiler flask to a receiver flask maintained at cooling water temperature of about 17° C. The overhead and bottoms products were analyzed by gas chromatography to determine the compositions. The resultant compositions and fractional recoveries and separations, representative of steady state operation are given in Table III. The temperatures given in Table III are in 0° C. at the top (Reflux Head) of the Oldershaw column and in the reboiler and for the 2-methylbutane/epoxybutene feed (Main Feed) and the feed of the extractive distillation solvent (Solvent Feed). The compositions of the condensed vaporous product (Overhead Comp) and the liquid product removed from the bottom of the column (Bottoms Comp) are given in Table III as weight percentages of 2-Methylbutane, Epoxybutene and the extractive distillation solvent (Solvent).

TABLE III

| | Example No. | | | |
| --- | --- | --- | --- | --- |
| | C-2 | 11 | 12 | 13 |
| Temperature | | | | |
| Reflux Head | 26.2 | 26.1 | 26.0 | 26.1 |
| Solvent Feed | — | 27.4 | 32.0 | 37.8 |
| Main Feed | 28.1 | 26.8 | 32.3 | 30.6 |
| Reboiler | 65.0 | 97.0 | 111.1 | 114.2 |
| Distillate Comp | | | | |
| 2-Methylbutane) | 98.8 | 100.0 | 99.9 | 99.7 |
| Epoxybutene | 1.2 | N/D | 0.1 | N/D |
| Solvent | — | N/D | N/D | 0.3 |
| Bottoms Comp | | | | |
| 2-Methylbutane | 3.9 | 3.0 | 0.7 | 0.2 |
| Epoxybutene | 96.1 | 11.8 | 11.2 | 12.7 |
| Solvent | — | 85.2 | 88.1 | 87.1 |
| Epoxybutene Recovery | 0.95 | 1.0 | 0.997 | 1.0 |
| 2-Methylbutane Removal | 0.99 | 0.94 | 0.98 | 0.995 |
| Fractional Recovery of Epoxybutene | 0.95 | 1.0 | 0.997 | 0.98 |
| Fractional Removal of 2-methylbutane | 0.99 | 0.94 | 0.98 | 0.995 |

N/D = none detected.

Example 14

Examples 14 demonstrates the separation and purification of epoxybutene from the liquid comprising epoxybutene and extractive distillation solvent removed from the lower section or base of the extractive distillation column (bottoms product). The bottoms product of Example 13, consisting approximately of 87.1 weight percent 1-methoxy-2-propyl acetate, less than 0.2 weight percent 2-methylbutane, and 12.7 weight percent epoxybutene was fed continuously to plate 25 (counting from the bottom) of a 65-plate, 1-inch diameter, vacuum jacketed Oldershaw column. The column was fitted with a 500 ml glass reboiler flask and boil-up was provided by a 500-watt electric resistive heating mantle fitted to the reboiler. Overhead vapors were condensed in a glass double-condenser (coolant jacket and interior coil) provided with a continuous supply of ice-chilled water. Reflux was provided by a magnetically-controlled plunger-type glass reflux head. The reflux timer was set to return condensed material to the column for 3 seconds out of every 18 seconds, or at a reflux ratio of 5 to 1. Overhead product was collected continuously in a refrigerated receiver flask maintained at 0° C. The bottoms product was pumped continuously from the reboiler flask to a receiver flask maintained at cooling water temperature of about 17° C. The feed and overhead and bottoms products were analyzed by gas chromatography to determine the compositions. The distillate was essentially pure epoxybutene as no 1-methoxy-2-propyl acetate and less than 0.2 weight percent 2-methylbutane was detected therein. The bottoms product consisted of 1.7 weight percent epoxybutene and 98.2 weight percent 1-methoxy-2-propyl acetate.

The invention has been described in detail with particular reference to preferred embodiments thereof, but it will be understood that variations and modifications can be effected within the spirit and scope of the invention.

We claim:

1. Process for the separation of 3,4-epoxy-1-butene (epoxybutene) from a mixture comprising epoxybutene and at least one aliphatic or aromatic hydrocarbon containing five to seven carbon atoms and having a boiling point of between about 20 and 115° C. which comprises the steps of:
   (1) feeding a mixture comprising epoxybutene and at least one hydrocarbon selected from aliphatic or aromatic hydrocarbons containing five to seven carbon atoms and having boiling points of between about 20 and 115° C., to the mid-section of an extractive distillation column;
   (2) feeding an extractive distillation solvent to the upper section of the extractive distillation column;
   (3) removing from the upper section or top of the extractive distillation column a vapor comprising the hydrocarbon;
   (4) removing from the lower section or base of the extractive distillation column a liquid comprising epoxybutene and extractive distillation solvent; and
   (5) separating the liquid of step (4) into epoxybutene and extractive distillation solvent; wherein the extractive distillation solvent (i) is inert, (ii) does not form an azeotrope with either epoxybutene or the hydrocarbon, (iii) is miscible with epoxybutene and the hydrocarbon, (iv) has a boiling point at least about 20° C. higher than the higher boiling point of epoxybutene and the hydrocarbon, and (v) creates a large relative volatility difference between epoxybutene and the hydrocarbon; and wherein the extractive distillation solvent is selected from the group consisting of C3 to C12 alcohols, C5 to C12 aliphatic ketones; alkyl alkanoate esters containing a total of 6 to 12 carbon atoms, C6 to C12 aliphatic and cyclic ethers, glycol ethers containing a total of 4 to 12 carbon atoms, glycol ether esters containing a total of 5 to 12 carbon atoms, polar aprotic solvents, and mixtures thereof.

2. The process of claim 1 wherein the extractive distillation solvent is selected from the group consisting of 1-methyl-2-pyrrolidinone, pyridine, dimethylformamide, dimethylacetamide, diethylformamide, diethylacetamide, acetonitrile, dimethylsulphoxide, morpholine, dibutylether, diisobutylether, diethylene glycol dimethyl ether, triethylene glycol dimethyl ether, tetraethylene glycol dimethyl ether, ethylene glycol monoethyl ether, ethylene glycol monobutyl ether, ethylene glycol monopropyl ether, propylene glycol monomethyl ether, propylene glycol monoethyl ether, propylene glycol monopropyl ether, diethylene glycol monomethyl ether, diethylene glycol monoethyl ether, diethylene glycol monopropyl ether, diethylene glycol monobutyl ether, ethylene glycol monoethyl ether acetate, ethylene glycol monobutyl ether acetate, ethylene glycol monopropyl ether acetate, propylene glycol monomethyl ether acetate, propylene glycol monoethyl ether acetate, propylene glycol monopropyl ether acetate, 2-heptanone, 3-heptanone, 4-heptanone, 6-methyl-2-hexanone, methylisobutylketone, diisopropylketone, dipropylketone, dibutylketone, cyclohexanone, diisobutylketone, isobutyl isobutyrate, n-butyl propionate, isobutyl propionate, n-propylbutyrate, isopropyl butyrate, isopropyl isobutyrate, n-butyl butyrate, 2-ethylhexyl acetate, methyl benzoate, isopentyl acetate, n-pentyl acetate, n-butyl acetate, propanol, n-butanol, n-pentanol, 2-pentanol, 3-pentanol, n-hexanol, cyclohexanol, and mixtures thereof.

3. Process according to claim 1 wherein the mass ratio of extractive distillation solvent feed to epoxybutene/hydrocarbon feed is about 10:1 to 1:3 and the extractive distillation solvent is selected from the group consisting of alkyl alkanoate esters containing 6 to 8 carbon atoms, C6 to C8 aliphatic ketones, C6 to C8 glycol ether acetates.

4. Process according to claim 1 wherein the mass ratio of extractive distillation solvent feed to epoxybutene/hydrocarbon feed is about 5:1 to 1:1 and the extractive distillation solvent is selected from the group consisting of 4-methyl-2-pentanone, 2-heptanone, 5-methyl-2-hexanone, n-butyl acetate, and propylene glycol monomethyl ether acetate.

5. Process for the separation of 3,4-epoxy-1-butene (epoxybutene) from a mixture comprising epoxybutene and at least one aliphatic or aromatic hydrocarbon containing five to seven carbon atoms and having a boiling point of between about 20 and 115° C. which comprises the steps of:
   (1) feeding a mixture comprising epoxybutene and at least one hydrocarbon selected from aliphatic or aromatic hydrocarbons containing five to seven carbon atoms and having boiling points of between about 20 and 115° C., to the mid-section of an extractive distillation column comprising 7 to 50 theoretical stages;
   (2) feeding an extractive distillation solvent to the upper section of the extractive distillation column;
   (3) removing from the upper section or top of the extractive distillation column a vapor comprising the hydrocarbon;
   (4) removing from the lower section or base of the extractive distillation column a liquid comprising epoxybutene and extractive distillation solvent; and
   (5) separating the liquid of step (4) into epoxybutene and extractive distillation solvent; wherein the extractive distillation solvent is selected from the group consisting of 4-methyl-2-pentanone, 2-heptanone, 5-methyl-2-hexanone, n-butyl acetate, and propylene glycol monomethyl ether acetate, the temperature at the top stage of the extractive distillation column is from about 10 to 90° C., the temperature at the base of the extractive distillation column is about 100 to 240° C., and the pressure within the extractive distillation column is about 0.1 to 4 bars absolute (bara).

6. Process according to claim 5 wherein the extractive distillation column comprises 10 to 35 stages, the temperature at the base of the extractive distillation column is about 100 to 180° C., and the pressure within the extractive distillation column is about 0.8 to 2 bara.

7. Process according to claim 5 wherein step (5) comprises the steps of:

(5) feeding the liquid comprising epoxybutene and the extractive distillation solvent removed from the lower section or bottom of the distillation column in step (4) to the mid-section of a solvent recovery distillation column;

(6) removing from the upper section or top of the solvent recovery distillation column a vaporous distillate product comprising greater than about 99.5 weight percent epoxybutene; and (7) removing from the lower section or bottom of the solvent recovery distillation column a liquid comprising the extractive distillation solvent.

8. Process according to claim 7 wherein the solvent recovery column comprises 3 to 20 theoretical stages, the temperature at the top stage of the solvent recovery column is from about 40 to 90° C., the temperature at the base of the extractive distillation column is about 100 to 240° C., and the pressure within the extractive distillation column is about 0.1 to 2 bars absolute (bara).

9. Process according to claim 7 wherein the solvent recovery column comprises 5 to 12 theoretical stages, the temperature at the top stage of the solvent recovery column is from about 40 to 90° C., the temperature at the base of the extractive distillation column is about 100 to 180° C., and the pressure within the extractive distillation column is about 0.15 to 1.0 bars absolute (bara).

* * * * *